(12) United States Patent
McCloskey

(10) Patent No.: US 10,086,069 B2
(45) Date of Patent: Oct. 2, 2018

(54) TREATMENT OF INFECTION

(71) Applicant: Jenny Colleen McCloskey, Mount Lawley (AU)

(72) Inventor: Jenny Colleen McCloskey, Mount Lawley (AU)

( * ) Notice: Subject to any disclaimer, the term of this patent is extended or adjusted under 35 U.S.C. 154(b) by 0 days.

(21) Appl. No.: 15/451,698

(22) Filed: Mar. 7, 2017

(65) Prior Publication Data

US 2017/0173148 A1 Jun. 22, 2017

Related U.S. Application Data

(63) Continuation of application No. 15/049,824, filed on Feb. 22, 2016, now abandoned, which is a continuation of application No. 14/156,533, filed on Jan. 16, 2014, now abandoned, which is a continuation of application No. 13/899,295, filed on May 21, 2013, now abandoned, which is a continuation of application No. 13/254,715, filed as application No. PCT/AU2010/000255 on Mar. 5, 2010, now abandoned.

(30) Foreign Application Priority Data

Mar. 5, 2009 (AU) .............................. 2009900969

(51) Int. Cl.

| | |
|---|---|
| *A61K 39/00* | (2006.01) |
| *A61K 39/12* | (2006.01) |
| *A61K 39/39* | (2006.01) |
| *A61K 39/02* | (2006.01) |
| *A61K 39/095* | (2006.01) |
| *A61K 9/00* | (2006.01) |
| *A61K 31/683* | (2006.01) |
| *A61K 33/08* | (2006.01) |
| *A61K 45/06* | (2006.01) |
| *A61K 31/661* | (2006.01) |
| *A61M 31/00* | (2006.01) |
| *C12N 7/00* | (2006.01) |

(52) U.S. Cl.
CPC ............ *A61K 39/39* (2013.01); *A61K 9/0014* (2013.01); *A61K 9/0031* (2013.01); *A61K 9/0034* (2013.01); *A61K 31/661* (2013.01); *A61K 31/683* (2013.01); *A61K 33/08* (2013.01); *A61K 39/12* (2013.01); *A61K 45/06* (2013.01); *A61M 31/00* (2013.01); *C12N 7/00* (2013.01); *A61K 2039/54* (2013.01); *A61K 2039/55505* (2013.01); *A61K 2039/55572* (2013.01); *A61M 2210/14* (2013.01); *C12N 2710/00034* (2013.01); *C12N 2710/20034* (2013.01)

(58) Field of Classification Search
CPC .. A61K 2300/00; A61K 31/683; A61K 33/08; A61K 2039/54; A61K 2039/55505
See application file for complete search history.

(56) References Cited

U.S. PATENT DOCUMENTS

| | | | |
|---|---|---|---|
| 5,776,468 | A | 7/1998 | Hauser et al. |
| 2002/0188242 | A1* | 12/2002 | Wu .................... A61N 1/327 604/21 |
| 2008/0226672 | A1 | 9/2008 | Garcon |
| 2012/0058149 | A1 | 3/2012 | McCloskey |
| 2013/0251753 | A1 | 9/2013 | McCloskey |
| 2014/0186406 | A1 | 1/2014 | McCloskey |
| 2016/0166682 | A1 | 2/2016 | McCloskey |

FOREIGN PATENT DOCUMENTS

| | | | |
|---|---|---|---|
| AU | 2010220824 | | 3/2010 |
| CA | 2754533 | | 3/2010 |
| EP | 10748238 | | 3/2010 |
| NZ | 595494 | | 3/2010 |
| WO | WO-1993/019780 A1 | | 10/1993 |
| WO | WO-1998/015287 A1 | | 4/1998 |
| WO | WO-2003/026681 A1 | | 4/2003 |
| WO | WO-2003/078455 A2 | | 9/2003 |
| WO | WO2004056389 | * | 7/2004 |
| WO | WO2006087563 | * | 8/2006 |
| WO | PCT/AU2010/000255 | | 3/2010 |
| WO | WO-2010/099580 A1 | | 9/2010 |

OTHER PUBLICATIONS

Didierlaurent, A.M. et al. (2009) AS04, an aluminum salt- and TLR4 agonist-based adjuvant system, induces a transient localized innate immune response leading to enhanced adaptive immunity. J Immunol. 183(10): 6186-97.

Giannini, S.L. et al. (2006) Enhanced humoral and memory B cellular immunity using HPV16/18 L1 VLP vaccine formulated with the MPL/aluminum salt combination (AS04) compared to aluminum salt only. Vaccine. 24(33-34): 5937-49.

Goto, N. et al. (1997) Local tissue irritating effects and adjuvant activities of calcium phosphate and aluminum hydroxide with different physical properties. Vaccine. 15(12-13): 1364-71.

Haidopoulos, D. et al. (2005) Can local application of imiquimod cream be an alternative mode of therapy for patients with high-grade intraepithelial lesions of the vagina? Int J Gynecol Cancer. 15(5):898-902.

Schiffman, M. et al. (2007) Human papillomavirus and cervical cancer. Lancet. 370(9590): 890-907.

(Continued)

*Primary Examiner* — Barry A Chestnut

(74) *Attorney, Agent, or Firm* — Ballard Spahr LLP

(57) ABSTRACT

The invention relates to compositions including a substance useful as an adjuvant for potentiating an immune response, and methods of using the composition in individuals with infections of tissue within or adjacent to a transformation zone, such as the transformation zone of the cervix or anal canal.

20 Claims, No Drawings

(56) References Cited

OTHER PUBLICATIONS

Extended European Search Report dated Oct. 19, 2010 for European Patent Application 10748238, which is a national phase application of PCT/AU2010/000255 filed on Mar. 5, 2010 (Applicant—Jenny Colleen McCloskey) (6 pages).
Examination Report mailed by the EPO dated Oct. 23, 2015 for European Patent Application 10748238, which is a national phase application of PCT/AU2010/000255 filed on Mar. 5, 2010 (Applicant—Jenny Colleen McCloskey) (5 pages).
Examination Report mailed by the EPO dated Apr. 7, 2017 for European Patent Application 10748238, which is a national phase application of PCT/AU2010/000255 filed on Mar. 5, 2010 (Applicant—Jenny Colleen McCloskey) (5 pages).
International Search Report dated May 31, 2010 for PCT/AU2010/000255 filed on Mar. 5, 2010, which was published as WO 2010/099580 on Sep. 10, 2010 (Applicant—Jenny Colleen McCloskey) (6 pages).
Written Opinion dated May 31, 2010 for PCT/AU2010/000255 filed on Mar. 5, 2010, which was published as WO 2010/099580 on Sep. 10, 2010 (Applicant—Jenny Colleen McCloskey) (6 pages).
International Preliminary Report on Patentability dated Sep. 6, 2011 for PCT/AU2010/000255 filed on Mar. 5, 2010, which was published as WO 2010/099580 on Sep. 10, 2010 (Applicant—Jenny Colleen McCloskey) (7 pages).
Examination Report dated Jun. 30, 2016 by the Canadian Intellectual Property Office for application CA 2,754,533, which is a national phase application of PCT/AU2010/000255 (Applicant—Jenny Colleen McCloskey) (4 pages).
Patent Examination Report dated Oct. 15, 2015 by the Australian Intellectual Property Office for application AU 2010220824, which is a national phase application of PCT/AU2010/000255 (Applicant—Jenny Colleen McCloskey) (3 pages).
First Examination Report dated Aug. 4, 2016 by the New Zealand Intellectual Property Office for application NZ 595494, which is a national phase application of PCT/AU2010/000255 (Applicant—Jenny Colleen McCloskey) (3 pages).
Preliminary Amendment filed on Sep. 2, 2011 for U.S. Appl. No. 13/254,715, which was filed Nov. 21, 2011 (Applicant/Inventor—Jenny Colleen McCloskey) (7 pages).
Requirement for Restriction or Election dated Aug. 28, 2012 for U.S. Appl. No. 13/254,715, which was filed Nov. 21, 2011 (Applicant/Inventor—Jenny Colleen McCloskey) (9 pages).
Response to Requirement for Restriction or Election filed on Oct. 28, 2012 for U.S. Appl. No. 13/254,715, which was filed Nov. 21, 2011 (Applicant/Inventor—Jenny Colleen McCloskey) (8 pages).
Non-Final Office Action dated Dec. 21, 2012 for U.S. Appl. No. 13/254,715, which was filed Nov. 21, 2011 (Applicant/Inventor - Jenny Colleen McCloskey) (9 pages).
Preliminary Amendment filed on May 21, 2013 for U.S. Appl. No. 13/899,295, which was filed May 21, 2013 (Applicant/Inventor—Jenny Colleen McCloskey) (6 pages).
Non-Final Office Action dated Jul. 18, 2013 for U.S. Appl. No. 13/899,295, which was filed May 21, 2013 (Applicant/Inventor—Jenny Colleen McCloskey) (13 pages).
Preliminary Amendment filed on Jan. 16, 2014 for U.S. Appl. No. 14/156,533, which was filed Jan. 16, 2014 (Applicant/Inventor—Jenny Colleen McCloskey) (3 pages).
Requirement for Restriction or Election dated May 14, 2015 for U.S. Appl. No. 14/156,533, which was filed Jan. 16, 2014 (Applicant/Inventor—Jenny Colleen McCloskey) (7 pages).
Response to Requirement for Restriction or Election filed on Sep. 14, 2015 for U.S. Appl. No. 14/156,533, which was filed Jan. 16, 2014 (Applicant/Inventor—Jenny Colleen McCloskey) (7 pages).
Non-Final Office Action dated Sep. 22, 2015 for U.S. Appl. No. 14/156,533, which was filed Jan. 16, 2014 (Applicant/Inventor—Jenny Colleen McCloskey) (12 pages).
Requirement for Restriction or Election dated Jul. 1, 2016 for U.S. Appl. No. 15/049,824, which was filed Feb. 22, 2016 (Applicant—Jenny Colleen McCloskey) (6 pages).
Response to Requirement for Restriction or Election dated Aug. 29, 2016 for U.S. Appl. No. 15/049,824, which was filed Feb. 22, 2016 (Applicant—Jenny Colleen McCloskey) (7 pages).
Non-Final Office Action dated Oct. 7, 2016 for U.S. Appl. No. 15/049,824, which was filed Feb. 22, 2016 (Applicant—Jenny Colleen McCloskey) (11 pages).
U.S. Appl. No. 13/254,715, filed Mar. 5, 2010, Jenny Colleen McCloskey, (2012/0058149), (Mar. 8, 2012).
U.S. Appl. No. 13/899,295, filed May 21, 2013, Jenny Colleen McCloskey, (2013/0251753), (Sep. 26, 2013).
U.S. Appl. No. 14/156,533, filed Jan. 16, 2014, Jenny Colleen McCloskey, (2014/0186406), (Jul. 3, 2014).
U.S. Appl. No. 15/049,824, filed Mar. 7, 2017, Jenny Colleen McCloskey, (2016/0166682), (Jun. 16, 2016).

* cited by examiner

TREATMENT OF INFECTION

The present application is a continuation of U.S. application Ser. No. 15/049,824 filed on Feb. 22, 2016, which is a continuation of U.S. application Ser. No. 14/156,533 filed on Jan. 16, 2014, which is a continuation of U.S. application Ser. No. 13/899,295 filed May 21, 2013, which is a continuation application of U.S. application Ser. No. 13/254,715 filed Nov. 21, 2011, which is a National Phase Application of International Application No. PCT/AU2010/000255 filed Mar. 5, 2010, which claims the benefit of priority to Australian Patent Application No. 2009900969 filed Mar. 5, 2009. The content of these earlier filed applications is hereby incorporated by reference in their entirety.

FIELD OF THE INVENTION

The invention relates generally to infections of tissue within or adjacent to a transformation zone, such as the transformation zones of the cervix and anus, especially infections by human papillomavirus (HPV). The invention also relates to adjuvants that have been used in vaccines against HPV including, but not limited to, AS04.

BACKGROUND OF THE INVENTION

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

The cervix is the lower, narrower portion of the uterus where it joins with the top end of the vagina. The exposed portion of the cervix that projects into the vagina is called the exocervix or ectocervix. The opening of the ectocervix is called the external os. Between the uterine cavity and the external os is a passageway known as the endocervical canal or the endocervix.

Generally two types of epithelium occur along the cervix. The position or location of these types may change due to cervical remodelling that occurs, for example, during puberty, menopause, pregnancy and child birth and the normal menstrual cycle.

In general, the ectocervix is covered by stratified squamous epithelium, whereas the endocervix is covered by simple columnar epithelium. The "squamocolumnar junction" is a region where the squamous epithelium is juxtaposed with the columnar epithelium. During times of cervical remodelling, the columnar epithelium of the endocervix may extend into the harsh acidic environment of the vagina and undergo metaplasia to hardier squamous epithelium. In turn, when the squamous epithelium regresses into the endocervical canal, the squamous epithelium is replaced by simple columnar epithelium. The area between the original squamocolumnar junction and the new squamocolumnar junction is termed the "transformation zone" (Rubin and Farber "Pathology". J.B. Lippincott Company 1988. Page 956). In teenage girls, the transformation zone is on the immature cervix's outer surface and is more susceptible to infection than in adult women. In older women, the transformation zone may be higher in the cervical canal.

Ectocervical epithelium consists of 4 layers: basal cells on the basal membrane; parabasal cells between the basal cell layer and the mature cell layers; a layer of intermediate, polygonal and mature cells; and superficial cells. A layer of exfoliating cells may also be seen in histological sections. Underneath the basal membrane is the connective tissue. The endocervical epithelium in contrast is a layer of columnar epithelium composed of mucin secreting cells on top of the connective tissue. The endocervical canal may contain crypt or crypt-like structures.

The transformation zone is itself particularly vulnerable to the effects of infections, the most well known one being infection with human papillomavirus (HPV). It has been estimated that 325 million women have either subclinical HPV or HPV-related clinical lesions. The presence of persistent HPV infection is thought to be a prerequisite for the development and maintenance of second and third stage cervical intraepithelial neoplasia (CIN II-III), i.e. severe or precancerous dysplasia. Cervical intraepithelial neoplasia (CIN) can be either squamous or glandular in origin, but squamous intraepithelial neoplasia (IN) is more common. CIN I represents mild IN and the cell abnormalities are confined to the basal ⅓ of the epithelium. CIN II is moderate IN confined to the basal ⅔ of the epithelium and CIN III is severe IN that spans more than ⅔ of the epithelium, possibly the full thickness.

Of the genital types affecting humans, the high-risk types such as HPV 16, HPV 18, HPV 45 and HPV 31 are linked to the development of low and high-grade dysplasia and cervical cancer. Oncogenic strains of HPV have been found in 99.7% of cervical cancers. They are also associated with vulval, anal and penile carcinoma. Low risk types such as HPV 6 and HPV 11 are associated with genital warts and low-grade IN.

Current treatment of severe uterine cervical IN is by surgically removing the areas of the uterine cervix that may possibly be involved. Treatment initially requires cytology, colposcopy and biopsy, and then a surgical treatment such as laser excision, loop excision or cold coagulation of the uterine cervix. These more radical treatments however are associated with increased risk of complications including cervical stenosis, constriction and complete sealing of the os, pelvic endometriosis following hematometra, painful and prolonged menstruation, excessive eversion of columnar epithelium, infection, bleeding, pain, psychological morbidity, infertility, and an incompetent cervix. And even after treatment, disease may recur and even progress to invasive cancer. Pre-term delivery is now also recognised as a complication.

In contrast, there is currently no reliable and effective treatment available for women who have been diagnosed with an HPV infection, usually during their routine Pap smears, but are asymptomatic or only have low grade lesions. The routine practice is to simply monitor the woman for signs of progression. This approach however is unsatisfactory for at least two reasons:

1. Some women are distressed by having Pap smear abnormalities even though they are not considered to be serious. In order to alleviate their concerns, many women with low-grade lesions undergo unnecessary treatment with the more radical methods reserved for severe IN.

2. In the absence of treatment, it is more difficult to ensure that the woman attends for further follow-up and monitoring for possible progression to high-grade disease.

There is therefore a need for a treatment of early stage infection before complications of infection occur. This treatment needs to be less invasive and radical than those currently available for the treatment of later stage disease.

In light of the vastness of the problem of HPV infection world wide, research has focused on prevention. This focus has seen the successful development of two vaccines—

Cervarix™, manufactured by GlaxoSmithKline, and Gardasil™ by Merck & Co. Cervarix™ is created using proteins of the HPV viral capsid, which once administered, induces the formation of neutralizing antibodies. In addition, Cervarix™ is formulated with AS04, a proprietary adjuvant that has been reported to boost the immune system response for a longer period of time by increasing the humoral immune response and increasing the number of immune memory B-cells (Vaccine 24, 14 Aug. 2006). AS04 is an adjuvant which is a combination of standard aluminium hydroxide and 3'-deacylated monophospholipid A (MPL—Corixa, Mo., USA), a derivative of the lipid A molecule found in gram-negative bacteria and a potent immune system stimulant.

Vaccines such as these however have two key limitations. The first is that Cervarix™ and Gardasil™ are both preventative vaccines, not therapeutic, and will therefore have no effect on already established infections. The second limitation is that HPV immunity is type-specific. So while these vaccines will block infection with the most common cancer causing HPV strains, vaccination with current vaccines will not completely block infection from cervical cancer-causing HPV strains other than HPV 16, 18, and in the case of Cervarix™, HPV 31 and 45 as well.

An object of the invention therefore is to endeavour to reduce the complications of HPV infection, the incidence of uterine cervical dysplasia (all stages) and cervical cancers, and to avoid more radical treatments by early treatment of infection.

It is understood that other tissues having transformation zones may also be more vulnerable to infection and would benefit from a treatment for early stage infection. The anus for example is also particularly vulnerable to the effects of HPV infection at the transformation zone where the stratified squamous cells of the anal verge change over to the columnar epithelial cells of the rectum. Current treatment for anal IN is either surgical removal or, in many cases, observational if severe focal or multi quadrant infection is present. It is observational in many cases where not extensive. If the dysplasia is very severe and involves the whole circumference of the anal canal, surgical treatment is to remove the whole area and provide a colostomy. Because the operation is so radical, and the duration of time to progress from anal dysplasia to anal cancer is not known, an observational approach is usually undertaken and the individual treated when cancer arises. This is obviously an unsatisfactory approach for individuals with early stage infection, who must simply sit back and wait to see if they develop cancer or other complications of HPV infection.

Other tissues susceptible to metaplasia and having transformation zones include the throat, where columnar epithelium is replaced by squamous epithelium, the oesophagus, where squamous epithelium is replaced by columnar epithelium, and the urinary bladder, where transitional epithelium is replaced by squamous epithelium.

It is also understood that infections of transformation zones may be by micro-organisms other than HPV. Other infections may include viral infection with herpes simplex virus (HSV), bacterial infections with *Chlamydia trachomatis, Haemophilus ducreyi, Mycoplasma hominis, Mycoplasma genitalium, Streptococcus* Sp, *Escherichia coli, Staphylococcus*, and *Neisseria gonorrhoeae*, fungal infections caused by an overgrowth of *Candida albicans* and other *Candida* species, protozoan infections with *Trichomonas vaginalis*.

In light of the different tissues that may require treatment of infection of the transformation zone, and the different micro-organisms that may be the infective agent, there is a need for a treatment that has broad application.

SUMMARY OF THE INVENTION

The invention seeks to at least minimise one or more of the above mentioned problems or limitations and in one embodiment provides a method for treating an infection in an individual. The method includes the steps of selecting an individual having an infection of tissue within or adjacent to a transformation zone; and contacting the tissue with a therapeutically effective amount of a composition including a substance useful as an adjuvant for potentiating an immune response, the substance being comprised of a combination of aluminium hydroxide and 3'-deacylated monophospholipid A, or aluminium hydroxide or 3'-deacylated monophospholipid A.

In another embodiment there is provided a method for treating an individual having a cervical HPV infection including the step of contacting infected tissue within or adjacent to the cervical transformation zone in the individual with a therapeutically effective amount of a composition including a substance useful as an adjuvant for potentiating an immune response, the substance being comprised of a combination of aluminium hydroxide and 3'-deacylated monophospholipid A.

In further embodiments there is provided a method of minimising the incidence of a complication of a cervical HPV infection in an individual including the step of selecting an individual having a cervical HPV infection and contacting infected tissue in or adjacent to a transformation zone in the individual with a therapeutically effective amount of a composition including a substance useful as an adjuvant for potentiating an immune response, the substance being comprised of a combination of aluminium hydroxide and 3'-deacylated monophospholipid A.

In other embodiments there is provided a therapeutic or pharmaceutical composition including a substance useful as an adjuvant for potentiating an immune response, the substance being comprised of a combination of aluminium hydroxide and 3'-deacylated monophospholipid A, the composition being characterised in that the composition does not include an immunogen for invoking an immune response.

In still further embodiments there is provided a kit or device including a composition described above.

In yet further embodiments there is provided a use of a composition as described above in the manufacture of means for treating an infection in an individual.

DETAILED DESCRIPTION OF THE EMBODIMENTS

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

It will be understood that the invention disclosed and defined in this specification extends to all alternative combinations of two or more of the individual features mentioned or evident from the text or drawings. All of these different combinations constitute various alternative aspects of the invention.

As used herein, except where the context requires otherwise, the term "comprise" and variations of the term, such as "comprising", "comprises" and "comprised", are not intended to exclude further additives, components, integers or steps.

As discussed herein, AS04 (which is composed of an aluminium salt and an immunostimulant, 3'-deacylated monophospholipid) and related compositions have been used in vaccines as an adjuvant for potentiating immune responses invoked by an immunogen contained in the vaccine to protect against viral infections. In these applications, the individual is normally one not having an infection.

The inventor has surprisingly found a new use for AS04 and related compositions in the form of a chemotherapy for the treatment of viral infections. Specifically, the inventor has found that a HPV infection can be cleared by administering AS04 and related compositions to tissue defining a cervical transformation zone.

Further, the inventor has found that an immunogen for invoking an immune response is not required. The finding is unanticipated as to date AS04 and related compositions have been administered simultaneously with an immunogen whereby the AS04 has potentiated an immune response raised against the immunogen, thereby preventing infection. Simply put, at the time of the invention, the therapeutic benefit of AS04 and like compositions had not been understood in the absence of an immunogen.

While not wanting to be bound by hypothesis, it is believed that when applied to tissue that is particularly vulnerable to infection, such as a transformation zone, AS04 or like compositions potentiate the response of local elements of the immune system to non-self antigen, leading to reduction or clearance of microbial load in infected individuals.

One advantage of the therapeutic composition is that the therapeutic benefit is not restricted to a particular organism, strain or serotype thereof, as for example is the case with a vaccine.

Further in combination with screening techniques for early detection of infection, with this invention it now becomes possible to effectively prevent complication of infection, such as cervical cancer.

Still further, in certain embodiments the therapeutic formulation does not include antigen, thereby minimising deleterious immune responses including auto-reactivity.

I. Definitions

AS04 is an adjuvant composed of an aluminium salt and an immunostimulant, 3'-deacylated monophospholipid A (MPL), and the names may be used interchangeably in the specification. The aluminium salt may be aluminium phosphate or preferably aluminium hydroxide. MPL is a purified, non-toxic endotoxin derivative of the lipopolysaccharide from a heptoseless mutant of *Salmonella minnesota*. The MPL can take the form of a mixture of related molecules, varying by their acylation. For example, the MPL may have 3, 4, 5 or 6 acyl chains, which may be of different length.

The skilled person will appreciate that the conventional terms "aluminium hydroxide" and MPL encompass variant molecules, and these are intended to be within the scope of the invention.

It will be understood that the term "transformation zone" refers to an area between an "original junction" defined by juxtaposed epithelial cells (juxtaposed in the sense of cells on one side having one form of histology and cells on the other side having another form) and a "new junction" (Rubin and Farber "Pathology". J. B. Lippincott Company 1988. Page 956). In one example, the junction is defined by squamous epithelial cells that are juxtaposed to columnar epithelial cells, as is seen in the cervix. With respect to the cervix, the "original junction" may be located on the exocervix, as in prenatal life or infancy. The "new junction" may be in the endocervical canal as in adult life.

The phrase "tissue within or adjacent to a transformation zone" refers to tissues, cells or extracellular matrix that is located at a region flanking a transformation zone, usually within a distance of no more than about 3 cm from a squamocolumnar junction, (or where a junction is formed from other epithelial cellular types, from within about 6 cm of that junction) and to tissues, cells or extracellular materials located in the epithelial layer, the basement membrane, lamina propria or underlying tissue in the immediate vicinity below the transformation zone. The tissue may include elements of the immune system such as lymphocytes, granulocytes antigen presenting cells and lymph nodes.

The phrase "contacting the tissue with a therapeutically effective amount of a composition including a substance useful as an adjuvant for potentiating an immune response" refers to a specific mode of administration whereby the composition is directly or locally applied or administered to tissue in or adjacent the relevant transformation zone. Such direct or local application or administration is to be distinguished from systemic administration of vaccine (such as Gardasil and Cervarix) as these vaccines have been generally used for preventing HPV infection.

A "therapeutic composition" or "pharmaceutical composition" or "composition for treating HPV infection" refers to a composition including a substance useful as an adjuvant for potentiating an immune response and which is a combination of aluminium hydroxide and 3'-deacylated monophospholipid A (the latter being a derivative of lipid A molecule found in gram negative bacteria). AS04 is one example.

The words "treat" or "treatment" refer to therapeutic treatment wherein the object is to slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Treatment may not necessarily result in the complete clearance of an infection but may reduce or minimise complications and side effects of infection and the progression of infection. The success or otherwise of treatment may be monitored by physical examination of the individual, cytopathological, DNA, or mRNA detection techniques.

The words "prevent" and "prevention" refer to prophylactic or preventative measures for protecting or precluding an individual not having a given infection related complication from progressing to that complication. Individuals in which prevention is required include those who have an infection.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) delays the onset of one or more symptoms of the particular disease, condition, or disorder described herein.

The term "package insert" is used to refer to instructions customarily included in commercial packages of therapeutic products, that contain information about the indications, usage, dosage, administration, contraindications and/or warnings concerning the use of such therapeutic products.

The phrase "pharmaceutically acceptable" indicates that the substance or composition must be compatible chemically and/or toxicologically, with the other ingredients comprising a formulation, and/or the mammal being treated therewith.

II. Methods of Treatment

In one embodiment there is provided a method for treating an infection in an individual. The method includes the steps of selecting an individual having an infection of tissue within or adjacent to a transformation zone; and contacting the tissue with a therapeutically effective amount of a composition including a substance useful as an adjuvant for potentiating an immune response, the substance being comprised of a combination of an aluminium salt and 3'-deacylated monophospholipid A. Preferably the aluminium salt is aluminium hydroxide (AH).

According to the method, the individuals to be treated are generally people having an infected tissue that defines a transformation zone. The individual may have other infected tissues, in the same organ or tissue containing the transformation zone or otherwise. The individual may be asymptomatic for the infection or present with sub clinical symptoms of infection.

Infection of tissue located in or adjacent to a transformation zone may be diagnosed by routine cytopathological techniques. Where the cervix is concerned, one example is pap smear where a sample of cells from the transformation zone of the cervix is taken, and the cells are reviewed for the presence of characteristic cellular changes. An HPV o infection may also be diagnosed by detection of HPV DNA. This test may be done on its own or as a complement to a pap smear, particularly when pap smear results are inconclusive. The Hybrid Capture™ 2 High-Risk HPV DNA test™ by Digene™ for example if an in vitro nucleic acid hybridisation assay for the qualitative detection of HPV 16, 18, 31, 33, 35, 45, 51, 52, 56, 58, 59 and 68 in cervical cell specimens or biopsy samples. To date, HPV cannot be readily cultured in vitro, and immunological tests are inadequate to determine the presence of HPV cervical infection.

Generally where the cervix is concerned, the individual has a microbial load according to the Digene Hybrid Capture 2 of at least 0.8 RLU.

In relation to anal HPV infection, diagnosis may be done by physical examination and by the presence of characteristic cellular changes associated with viral replication in biopsy specimens.

The infection may be present in the transformation zone of the cervix or the anus, or for female individuals, both.

The individual in need of treatment may have one or more infections including opportunistic infections of viral, bacterial, fungal and protozoan origin. For example, *Chlamydia trachomatis* is frequently associated with benign proliferative, pre-neoplastic and malignant changes in cervical epithelium, and may therefore be present as a co-infection with HPV. Herpes simplex virus (HSV) is also a common co-infection with HPV due to their similar means of transmission. It is envisaged that the method of the invention will be useful in treating both infections due to the non-organism specific nature of the adjuvant. However other therapeutics may be co-administered.

Immunosuppressed individuals such as those receiving transplant therapy or those having HIV infection are contemplated as individuals to whom the methods of the invention may be applied.

The therapeutic or pharmaceutical composition for use in these methods of treatment are described further below. In one embodiment, the composition for use in these methods may contain aluminium hydroxide and 3'-deacylated monophospholipid A as the only active ingredients in which case the composition may not include an immunogen for invoking an immune response against an antigen that is associated with the disease or condition that is to be treated by the composition. When the infected tissue is in the cervix, the composition of the invention is preferably contacted with the infected tissue of the endocervical canal of the cervix.

In an alternative embodiment the composition may further include a polypeptide provided in the form of an immunogen, especially a polypeptide that defines, or is contained, or is comprised in a microbial antigen such as a viral antigen, bacterial antigen, fungal antigen or protozoan antigen. Examples of suitable therapeutic compositions according to these embodiments include Cevarix and Gardasil containing HPV antigens. In one embodiment, the composition may also be formulated with an antigen derived from HPV, provided that the antigen is not derived from HPV subtypes 6, 11, 16, 18, 45 and 31.

According to the invention, the tissue in or adjacent to the transformation zone is contacted with the therapeutic or pharmaceutical composition so that at least some, if not all of the various elements of the zone are brought into contact with, or exposed to the composition. In certain embodiments, elements of the immune system, such as one or more of lymphocytes, granulocytes and/or antigen presenting cells (APCs) that are localised about the zone are brought into contact with the composition.

In other embodiments the therapeutic or pharmaceutical composition is applied to the endocervical canal and/or the transformation zone.

The composition may be applied to the apical surface of the epithelial cells in conditions where the substance may infuse cell junctures. Alternatively, the visceral surface of the transformation zone may be slightly abraded or ruptured resulting in the removal of some or all of the epithelial cells, basement membrane and lamina propria. It is also envisaged that the composition may be directly injected into the tissue of the transformation zone.

It will be clear that the intention is for treatment of infected cells within and adjacent to the transformation zone, and that in certain embodiments the methods of the invention include a step of selecting an individual having an infection of tissue within or adjacent to a transformation zone.

The step of contacting the tissue with a therapeutically effective amount of the composition may be achieved in a number of ways. In a preferred embodiment, the adjuvant is applied using the apparatus described in WO2003/026681 (McCloskey), the contents of which are herein incorporated in their entirety by reference. The apparatus for treatment of early human papillomavirus infection of an orifice of a human or animal body including any canal associated with the orifice, comprises a stem means adapted for insertion along the orifice or canal; means carried by the stem means for occluding a distal restriction whereby to define a treatment cavity in the orifice and/or canal; and means to deliver an effective amount of an agent for inactivation of papillomavirus to said treatment cavity for application to the surfaces of the orifice and/or canal bounding said cavity.

The method of treatment described herein may conveniently be implemented as a post surgical procedure.

The adjuvant is to be used in a therapeutically effective amount. The therapeutically effect amount in certain embodiments is about 0.1 to 1 mg of Al (OH)$_3$ or any amount within that range including 0.1, 0.15, 0.2, 0.25, 0.3, 0.35, 0.4, 0.45, 0.5, 0.55, 0.6, 0.65, 0.7, 0.75, 0.8, 0.85, 0.9, 0.95 and 1 mg and 1 to 100 μg of MPL, or any amount within that range including 1, 2, 3, 4, 5, 6, 7, 8, 9, 10 ,11,12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 ,53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100 μg. Where Cevarix is used the dose may be about 0.5 mL.

Generally the therapeutic composition is administered twice daily, daily, once weekly or monthly until the infection has been cleared.

Progress of treatment may be monitored using the same techniques as diagnosis. That is, cytological examination of cells from the transformation zone and/or detection of viral DNA in the cells obtained by pap smear or biopsy, or in secretions from infected tissue. Treatment may also be resumed in the event of re-infection occurring.

In another embodiment there is provided a method for treating an individual having a cervical HPV infection including the step of contacting infected tissue within or adjacent to the cervical transformation zone in the individual with a therapeutically effective amount of a composition including a substance useful as an adjuvant for potentiating an immune response, the substance being comprised of a combination of aluminium hydroxide and 3'-deacylated monophospholipid A.

In further embodiments there is provided a method of minimising the incidence of a complication of a cervical HPV infection in an individual including the step of selecting an individual having a cervical HPV infection and contacting infected tissue in or adjacent to a transformation zone in the individual with a therapeutically effected amount of a composition including a substance useful as an adjuvant for potentiating an immune response, the substance being comprised of a combination of aluminium hydroxide and 3'-deacylated monophospholipid A. The aluminium hydroxide and 3'-deacylated monophospholipid A may constitute the only active ingredients in the composition. Alternatively, additional active ingredients may be included, including immunogens such as viral antigens.

When the infected tissue is in the cervix, the composition of the invention is preferably applied to the endocervical canal of the cervix.

III. Compositions and Formulations

As described herein, the invention relates to a therapeutic or pharmaceutical composition including a substance useful as an adjuvant for potentiating an immune response, the substance being comprised of a combination of aluminium hydroxide and 3'-deacylated monophospholipid A. Typically, the composition is characterised in that the composition does not include an immunogen for invoking an immune response against the aetiological agent of the disease or condition to be treated.

The composition may further comprises a pharmaceutically acceptable diluent, carrier, excipient or like compound. Acceptable diluents, carriers, excipients, and stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as plasma albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The composition may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable, examples of sustained-release preparations include semipermeable matrices of solid hydrophobic polymers containing the N-acylated dipeptide proline boronate compound, which matrices are in the form of shaped articles, e.g. films, or microcapsules. Examples of sustained-release matrices include polyesters, hydrogels (for example, poly(2-hydroxyethyl-methacrylate), or polyCvinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

Compositions prepared for various routes and types of administration may be in suitable or useful form for application to the transformation zone in certain embodiments of the invention. The substance useful as an adjuvant for potentiating an immune response being comprised of a combination of aluminium hydroxide and 3'-deacylated monophospholipid A and having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. In general the formulations are prepared by uniformly and intimately bringing into association the active ingredient with liquid carriers or finely divided solid carriers or both, and if necessary, shaping the product. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment. The inhibitory compound for use herein is preferably sterile. The compound ordinarily will be stored as a solid composition, although lyophilized formulations or aqueous solutions are acceptable. Thus in certain embodiments there is provided a use of a composition as described above in the manufacture of a composition for treating an infection in an individual.

The composition may be packaged in a variety of ways depending upon the method used for administering the drug. Generally, a kit or article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

In certain embodiments, the therapeutic composition consists essentially of a substance useful as an adjuvant for potentiating an immune response and which is a combination of aluminium hydroxide and 3'-deacylated monophospholipid A. By "consists essentially of" it is meant that the composition does not include any other active ingredient or principal. In these embodiments, the therapeutic composition may contain diluents, excipients, fillers and the like as described above.

In other embodiments, the therapeutic composition does not contain a molecule provided in the form of an immunogen. Thus for example, in these embodiments, the therapeutic composition does not contain a polypeptide forming an antigen on a microorganism such as a virus or bacteria.

In other embodiments, the therapeutic composition further includes a further active pharmaceutical or principle. These may be incorporated into the therapeutic composition, depending on the anticipated route of administration and the stage of the infection or related complications. In the case of co-infections, the therapeutic composition may include one or more anti-viral, anti-bacterial, anti-fungal and anti-protozoan agents. As well as treating the infection in the transformation zone itself, treatment of side effects from infection may be undertaken. For example, the therapeutic composition may further include an anti-inflammatory to treat inflammation as the site of infection. In the event that there is mild irritation or discomfort associated with the lesions associated with the HPV infection, or the procedure by which the therapeutic composition is to be applied, the composition may further include an analgesic.

The pharmaceutical composition may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

The composition of the invention may be formulated as an ointment, cream, gel or lotion. Ointments and creams may, for example, be formulated with an aqueous or oily base with the addition of suitable thickening and/or gelling agents. Lotions and gels may be formulated with an aqueous or oily base, and will in general also contain one or more emulsifying agents, stabilising agents, dispersing agents, suspending agents, thickening agents, or colouring agents.

Compositions of the invention formulated for vaginal administration may be presented as pessaries, tampons, creams, gels, pastes, foams, injectable solution or sprays containing in addition to the adjuvant such carriers as are known in the art to be appropriate. Accordingly the invention provides a topical composition including a substance useful as an adjuvant for potentiating an immune response, the substance being comprised of a combination of a therapeutically effective amount of aluminium hydroxide and 3'-deacylated monophospholipid A (MPL); and a pharmaceutically acceptable diluent or carrier, the composition being characterised in that the composition does not include an immunogen for invoking an immune response. The topical composition of the invention may be contacted with infected tissue within or adjacent to a transformation zone of an individual. In a preferred embodiment, the tissue is infected with HPV.

Formulations for topical administration include one or more of the following ingredients together with the therapeutically effective amount of aluminium hydroxide and 3'-deacylated monophospholipid A (MPL); sodium chloride, L-histidine, sodium borate, lactic acid, sodium phosphate monobasic, sorbitan monostearate, polysorbate 60, cetyl esters wax, benzyl alcohol, glycerol, cetostearyl alcohol, isopropyl myristate, propylene glycol, purified water, chlorohexidine hydrochloride octyldodecanol, sodium hydroxide, stearic acid and paraffin liquid.

Compositions of the invention formulated for rectal administration wherein the carrier is a solid are most preferably presented as unit dosage suppositories. Suitable carriers include cocoa butter, water soluble based carriers such as polyethylene glycol, and glycerin and other materials commonly used in the art. The suppositories may be conveniently formed by admixture of the adjuvant with the softened or melted carrier(s) followed by chilling and shaping moulds.

It is especially advantageous to formulate the compositions of the present invention in unit dosage form for ease of administration and uniformity of dosage. The specifications for the dosage unit forms of the present invention may be determined by a person skilled in the art depending on, for example (a) the characteristics of the adjuvant and the particular therapeutic effect to be achieved, and (b) the limitations inherent in the art of compounding such an active ingredient for the particular treatment.

The adjuvant composition may also be formulated for administration by injection directly in to the infected cells of the tissue, for example bolus injection, or continuous infusion, and may be presented in unit dosage form in ampoules, pre-filled syringes, small volume infusion or in multi-dose containers with an added preservative. The compositions may take such forms as suspensions, solutions, or emulsions in oily or aqueous vehicles, and may contain formulating agents such as suspending, stabilising and/or dispersing agents.

Alternatively, the adjuvant may be in powder form, obtained by aseptic isolation of sterile solid or by lyophilisation from solution, for constitution with a suitable vehicle, e.g. sterile, pyrogen-free water, before use.

IV. Kits

In other embodiments there is provided a kit for use in one of the above described embodiments, the kit including:

a container holding a therapeutic composition;

a label or package insert with instructions for use.

In certain embodiments the kit may contain one or more further active principles or ingredients for treatment or an infection or for preventing an infection-related complication described above.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds a therapeutic composition which is effective for treating the condition and may have a sterile access port (for example the container may be an intravenous solution bag or a vial having a stopper pierceable by a hypodermic injection needle). The label or package insert indicates that the therapeutic composition is used for treating the condition of choice. In one embodiment, the label or package insert includes instructions for use and indicates that the therapeutic composition can be used to treat an infection or to prevent a complication stemming from infection.

The kit may comprise (a) a therapeutic composition; and (b) a second container with a second active principle or ingredient contained therein. The kit in this embodiment of the invention may further comprise a package insert indicating that the other active principle can be used to treat a disorder or prevent a complication stemming from infection. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

V. Devices

In certain embodiments the therapeutic composition may be provided in the form of a device, disposable or reusable, including a receptacle for holding the therapeutic composition. In one embodiment, the device is a syringe. The device may hold 1-2 mL of the therapeutic composition. The therapeutic composition may be provided in the device in a state that is ready for use or in a state requiring mixing or addition of further components.

EXAMPLES

Exemplary compositions for formulation as a topical composition.

i)

|  | Range | Preferred (0.5 mL dose) |
|---|---|---|
| Al (OH)$_3$ | 200-550 µg | 0.5 mg |
| MPL | 20-100 µg | 50 µg |
| NaCl | 3-10 mg | 4.4 mg |
| NaH$_2$PO$_4$•2H$_2$O | 500-700 µg | 624 µg |

Adjusted to a pH of between 6 and 8 and to be formulated into a cream for topical application.

ii)

|  | Range | Preferred (0.5 mL dose) |
|---|---|---|
| Al (OH)$_3$ | 200-550 µg | 225 µg |
| MPL | 20-100 µg | 50 µg |
| NaCl | 3-10 mg | 9.56 mg |
| L-histidine | 0.5-1 mg | 0.78 mg |
| Polysorbate 60 | 20-100 µg | 50 µg |
| NaBr | 25-50 µg | 35 µg |

Adjusted to a pH of between 6 and 8 and to be formulated into a cream for topical application.

iii)

|  | Range | Preferred (0.5 mL dose) |
|---|---|---|
| HPV antigen | 20-40 µg | 20 µg of each different antigen |
| Al (OH)$_3$ | 200-550 µg | 0.5 mg |
| MPL | 20-100 µg | 50 µg |
| NaCl | 3-10 mg | 4.4 mg |
| NaH$_2$PO$_4$•2H$_2$O | 500-700 µg | 624 µg |

The HPV antigen may be selected from one or more of 6, 11, 16, 18, 30, 31, 33, 35, 39, 42, 43, 44, 45, 51-56, 58, 59, 66 and 68, but usually one or more of 6, 11, 16, 18, 45 and 56. Adjusted to a pH of between 6 and 8 and to be formulated into a cream for topical application.

iv)

|  | Range | Preferred (0.5 mL dose) |
|---|---|---|
| HPV antigen | 20-40 µg | 20 µg of each different antigen |
| Al (OH)$_3$ | 200-550 µg | 225 µg |
| MPL | 20-100 µg | 50 µg |
| NaCl | 3-10 mg | 9.56 mg |
| L-histidine | 0.5-1 mg | 0.78 mg |
| Polysorbate 60 | 20-100 µg | 50 µg |
| Na borate | 25-50 µg | 35 µg |

The HPV antigen may be selected from one or more of 6, 11, 16, 18, 30, 31, 33, 35, 39, 42, 43, 44, 45, 51-56, 58, 59, 66 and 68, but usually one or more of 6, 11, 16, 18, 45 and 56. Adjusted to a pH of between 6 and 8 and to be formulated into a cream for topical application.

v) Exemplary Topical Composition Ingredients Selected From:

| | | |
|---|---|---|
| Lactic acid | Sorbitan monostearate | Polysorbate 60 |
| Cetyl esters wax | Cetostearyl alcohol | Isopropyl myristate |
| Benzyl alcohol | Purified water | Octyldodecanol |
| Glycerol | Chlorhexidine hydrochloride | Sodium hydroxide |
| Propylene glycol | Paraffin liquid | Stearic acid | vi) Pessary Formulations Further Include:

| | |
|---|---|
| Lactose | Calcium lactate pentahydrate |
| Maize starch | Silica-colloidal anhydrous |
| Magnesium stearate | Cellulose microcrystalline |
| Crospovidone | Hypermellose |
| Lactic acid | |

The invention claimed is:

1. A method for inducing an immune response in an individual, the method comprising administering to an individual with a HPV infection an effective amount of a composition consisting of aluminium hydroxide and 3' deacylated monophospholipid A; and a pharmaceutically acceptable diluent, carrier, excipient or stabilizer; wherein the composition induces an immune response in the individual with the HPV infection.

2. The method of claim 1, wherein the individual having the HPV infection of tissue is selected on the basis of cellular changes in a sample from a transformation zone of the individual, physical examination or by detection of nucleic acid of an agent causing the HPV infection.

3. The method of claim 1, wherein the HPV infection is in a transformation zone.

4. The method of claim 3, wherein the transformation zone is abraded or ruptured prior to contacting the infected tissue within or adjacent to the transformation zone.

5. The method of claim 1, wherein the composition is brought into contact with the infected tissue by means of an apparatus, wherein the apparatus comprises a stem means adapted for insertion along an orifice or canal to access a transformation zone; means carried by the stem means for occluding a distal restriction; and means to deliver an effective amount of the composition to the infected tissue.

6. The method of claim 1, wherein the composition is brought into contact with a surface of the infected tissue by direct application to the surface or injection of the composition into cells at the surface of the infected tissue.

7. The method of claim 1, wherein the method further comprises selecting an individual having a HPV infection of tissue within or adjacent to a transformation zone.

8. The method of claim 1, wherein administering is contacting a transformation zone with the composition.

9. A method of minimizing the incidence of a complication of a cervical or anal HPV infection in an individual, the method comprising selecting an individual having a cervical or anal HPV infection and contacting infected tissue in or adjacent to a transformation zone in the individual with a therapeutically effective amount of a composition consisting of aluminium hydroxide and 3'-deacylated monophospholipid A; and a pharmaceutical acceptable diluent, carrier, excipient or stabilizer; wherein the composition induces an immune response in an individual having a cervical or anal HPV infection and minimizes the incidence of a complication of a cervical or anal HPV infection in the individual.

10. The method of claim 9, wherein the individual having an infection of tissue is selected on the basis of cellular changes in a sample from the transformation zone of the individual, physical examination or by detection of nucleic acid of an agent causing the infection.

11. The method of claim 9, wherein the infection is in the transformation zone.

12. The method of claim 9, wherein the transformation zone is abraded or ruptured prior to contacting the infected tissue within or adjacent to the transformation zone.

13. The method of claim 9, wherein the composition is brought into contact with a surface of the infected tissue by direct application to the surface or injection of the composition into cells at the surface of the infected tissue.

14. A method for treating an individual having a cervical or anal HPV infection, the method comprising contacting infected tissue within or adjacent to a cervical or anal transformation zone in the individual having a cervical or anal HPV infection with a therapeutically effective amount of a composition consisting of aluminium hydroxide and 3'-deacylated monophospholipid A; and a pharmaceutically acceptable diluent, carrier, excipient or stabilizer; wherein the composition induces an immune response in the individual having a cervical or anal HPV infection.

15. The method of claim 14, wherein the transformation zone is abraded or ruptured prior to contacting the infected tissue within or adjacent to the transformation zone.

16. The method of claim 14, wherein the composition is brought into contact with the surface of the infected tissue by direct application to the surface or injection of the composition into cells at the surface of the infected tissue.

17. The method of claim 3, wherein the transformation zone is in the cervix or anus.

18. The method of claim 1, wherein composition is topically administered.

19. The method of claim 9, wherein composition is topically administered.

20. The method of claim 14, wherein composition is topically administered.

* * * * *